(12) United States Patent
Brännvall et al.

(10) Patent No.: US 9,045,378 B2
(45) Date of Patent: Jun. 2, 2015

(54) DENTAL APPLICATION COATING

(75) Inventors: Petrus Brännvall, Gothenburg (SE); Håkan Lindstrom, Vastra Frolunda (SE); Erik Adolfsson, Gothenburg (SE)

(73) Assignee: Nobel Biocare Services AG, Zurich-Flughafen (CH)

( * ) Notice: Subject to any disclaimer, the term of this patent is extended or adjusted under 35 U.S.C. 154(b) by 637 days.

(21) Appl. No.: 13/378,951

(22) PCT Filed: Jun. 17, 2010

(86) PCT No.: PCT/EP2010/003636
§ 371 (c)(1),
(2), (4) Date: Feb. 17, 2012

(87) PCT Pub. No.: WO2010/145822
PCT Pub. Date: Dec. 23, 2010

(65) Prior Publication Data
US 2012/0156472 A1 Jun. 21, 2012

(30) Foreign Application Priority Data
Jun. 19, 2009 (EP) .................................... 09008015

(51) Int. Cl.
B32B 18/00 (2006.01)
B05D 3/02 (2006.01)
B05D 7/00 (2006.01)
B32B 9/00 (2006.01)
B32B 3/00 (2006.01)
C04B 41/50 (2006.01)
C04B 41/00 (2006.01)
C04B 41/52 (2006.01)
C04B 41/87 (2006.01)
C04B 41/89 (2006.01)
A61K 6/02 (2006.01)
A61C 8/00 (2006.01)
C04B 111/00 (2006.01)

(52) U.S. Cl.
CPC ........... C04B 41/5042 (2013.01); A61C 8/0012 (2013.01); C04B 41/009 (2013.01); C04B 41/52 (2013.01); C04B 41/87 (2013.01); C04B 41/89 (2013.01); C04B 2111/0025 (2013.01); C04B 2111/00836 (2013.01); A61K 6/024 (2013.01); A61K 6/025 (2013.01)

(58) Field of Classification Search
CPC ..................................................... C04B 1/5042
See application file for complete search history.

(56) References Cited

U.S. PATENT DOCUMENTS

| | | | |
|---|---|---|---|
| 3,091,014 A | 5/1963 | Smoot et al. | |
| 3,421,914 A | 1/1969 | Hare | |
| 4,073,999 A | 2/1978 | Bryan et al. | |
| 4,892,846 A | 1/1990 | Rogers et al. | |
| 4,983,182 A * | 1/1991 | Kijima et al. | 424/423 |
| 5,080,589 A | 1/1992 | Oden et al. | |
| 5,106,303 A | 4/1992 | Oden et al. | |
| 5,192,325 A | 3/1993 | Kijima et al. | |
| 5,342,201 A | 8/1994 | Oden | |
| 5,902,429 A | 5/1999 | Apte et al. | |
| 5,961,329 A | 10/1999 | Stucki-McCormick | |

(Continued)

FOREIGN PATENT DOCUMENTS

| | | |
|---|---|---|
| DE | 4114792 A1 | 11/1992 |
| EP | 0 129 188 A2 | 12/1984 |

(Continued)

OTHER PUBLICATIONS

Machine translation of WO 03/035014, Theil et al. May 2003.*

(Continued)

Primary Examiner — David Sample
(74) Attorney, Agent, or Firm — Knobbe, Martens, Olson & Bear LLP

(57) ABSTRACT

The invention relates to a dental application body, comprising an oxide ceramic, containing a bulk material containing an oxide ceramic, preferably a zirconium oxide, and at least one coating containing an yttrium oxide and/or cerium oxide stabilized zirconium oxide, wherein the content of the stabilizing compound ($c_{[yttrium\ oxide]}$, $C_{[cerium\ oxide]}$) within the coating with respect to the zirconium oxide (in mol-%) satisfies the formula $c_{[yttrium\ oxide]} + 0.6 \times c_{[cerium\ oxide]} \geq 4$. Furthermore, the invention relates to a method for producing such a dental application body comprising the steps of providing a bulk material containing an oxide ceramic, preferably a zirconium oxide having a tetragonal microstructure as a main phase, and applying at least one coating containing an yttrium oxide and/or cerium oxide stabilized zirconium oxide, wherein the content of the stabilizing compound ($C_{[yttrium\ oxide]}$, $C_{[cerium\ oxide]}$) within the coating with respect to the zirconium oxide (in mol-%) satisfies the formula $c_{[yttrium\ oxide]} + 0.6 \times c_{[cerium\ oxide]} \geq 4$.

19 Claims, 11 Drawing Sheets

(56) References Cited

U.S. PATENT DOCUMENTS

| | | |
|---|---|---|
| 6,086,948 A | 7/2000 | Roth et al. |
| 6,149,688 A | 11/2000 | Brosnahan et al. |
| 6,534,197 B2 | 3/2003 | Noda et al. |
| 7,077,391 B2 | 7/2006 | Filser et al. |
| 7,223,356 B2 | 5/2007 | Chartier et al. |
| 8,231,825 B2 | 7/2012 | Eriksson et al. |
| 2004/0119180 A1 | 6/2004 | Frank |
| 2005/0106534 A1 | 5/2005 | Gahlert |
| 2005/0113834 A1 | 5/2005 | Breitenstien et al. |
| 2005/0187638 A1* | 8/2005 | Glien et al. ............ 623/23.56 |
| 2006/0009344 A1 | 1/2006 | Sone et al. |
| 2006/0174653 A1 | 8/2006 | Salomonson et al. |
| 2006/0246397 A1 | 11/2006 | Wolf |
| 2008/0213725 A1 | 9/2008 | Adilstam et al. |
| 2010/0291509 A1 | 11/2010 | Berggren et al. |
| 2010/0323327 A1 | 12/2010 | Eriksson et al. |
| 2011/0003083 A1* | 1/2011 | Yang et al. ................ 427/453 |
| 2011/0006451 A1 | 1/2011 | Adilstam et al. |
| 2011/0014586 A1 | 1/2011 | Jorneus et al. |
| 2012/0326343 A1 | 12/2012 | Eriksson et al. |

FOREIGN PATENT DOCUMENTS

| | | |
|---|---|---|
| EP | 328041 B * | 8/1989 |
| EP | 1 025 829 A1 | 8/2000 |
| EP | 1 396 237 | 3/2004 |
| EP | 1 210 054 B1 | 8/2004 |
| EP | 1450722 B1 | 9/2004 |
| JP | 60-60980 | 4/1985 |
| JP | 61-146757 | 7/1986 |
| JP | 63-156063 | 6/1988 |
| JP | 3186272 | 8/1991 |
| JP | 7275276 | 10/1995 |
| JP | 7323038 | 12/1995 |
| JP | 08-33701 | 2/1996 |
| JP | 8038512 | 2/1996 |
| JP | 2001-231849 | 8/2001 |
| JP | 2005-97094 | 4/2005 |
| JP | 2005-510493 | 4/2005 |
| JP | 2008-284349 | 11/2008 |
| WO | WO 95/35070 A1 | 12/1995 |
| WO | WO 99/50480 A1 | 10/1999 |
| WO | WO 01/34056 A1 | 5/2001 |
| WO | WO 2005/027771 A1 | 3/2005 |
| WO | WO 2008/013099 | 1/2008 |

OTHER PUBLICATIONS

Chevalier, Jérôme et al., "Critical effect of cubic phase on aging in 3 mol-%-yttria-stablized zirconia ceramics for hip replacement prosthesis," *Biomaterials,* vol. 25, pp. 5539-5545 (2004).

International Search Report for Application No. PCT/EP2010/003636 (the PCT counterpart of this application) mailed on Oct. 26, 2010 in 3 pages.

International Preliminary Report on Patentability for Application No. PCT/EP2010/003636 (the PCT counterpart of this application) issued on Dec. 20, 2011 in 5 pages.

English translation of Office Action for counterpart JP Application 2012-515393 mailed Jul. 4, 2014.

X. Balmes, "From dream to reality," in Spectrum Dialogue, vol. 6, No. 1, Seiten 52-66, Jan 1997.

International Search Report for Application No. PCT/SE2004/001279 (the PCT counterpart of U.S. Appl. No. 10/573,534) dated Dec. 22, 2004.

Zirkonium Implantate. Various enclosures from Prof. Dr. Sami Sandhaus to Frau Marina Andriotelli, www.incermed.de, Jul. 4, 2005.

Zalkind, DMD et al. "Dental Technology—Direct core buildup using a performed crown and prefabricated zirconium oxide post", *The Journal of Prosthetic Dentistry,* vol. 80, Issue 6, Dec. 1998.

Kohavi, DMD et al. "Adsorption of salivary proteins onto prosthetic titanium components", *The Journal of Prosthetic Dentistry,* vol. 74, Issue 5, Nov. 1995.

Wang, DDS, MSD et al. "Joining titanuim materials with tungsten inert gas welding, laser welding, and infrared brazing", *The Journal of Prosthetic Dentistry,* vol. 74, Issue 5, Nov. 1995.

Sandhaus et al. "Utilisation de la Zircone en implantologie: l'mplantat Sigma dáprès Sandhaus", Implantodontie, No. 27.

* cited by examiner

I
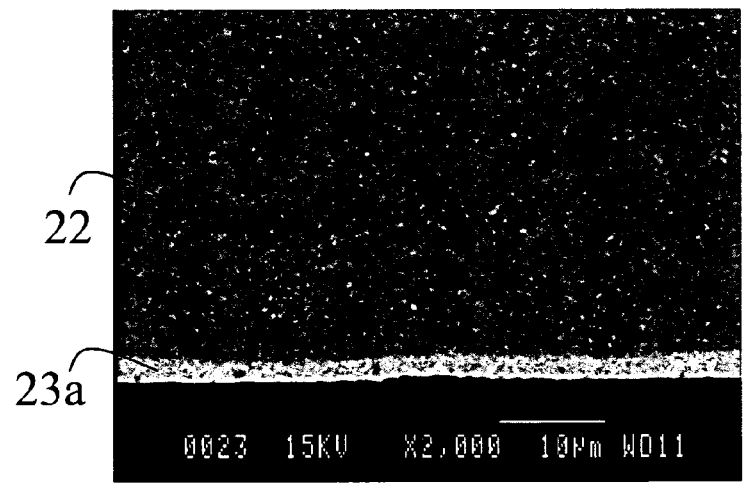
II
Fig. 2a:1

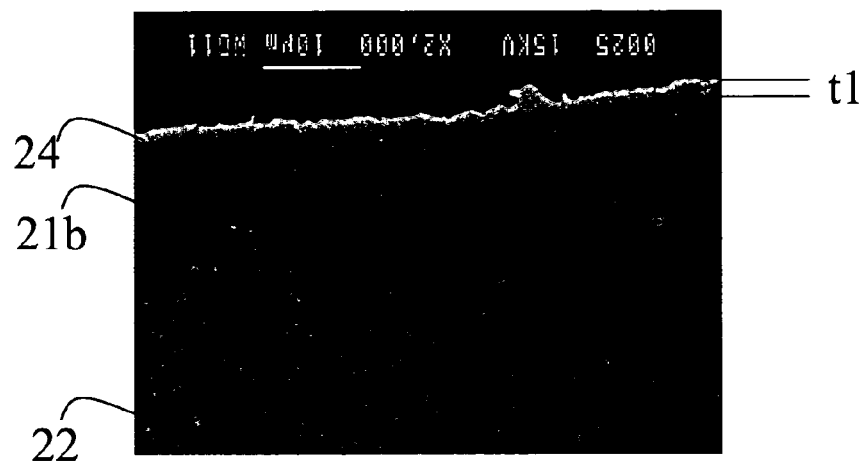
III
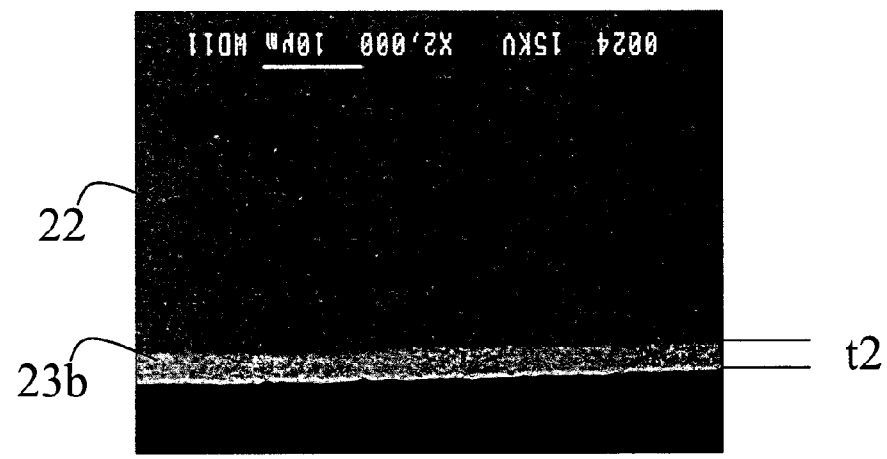
IV
Fig. 2a:2

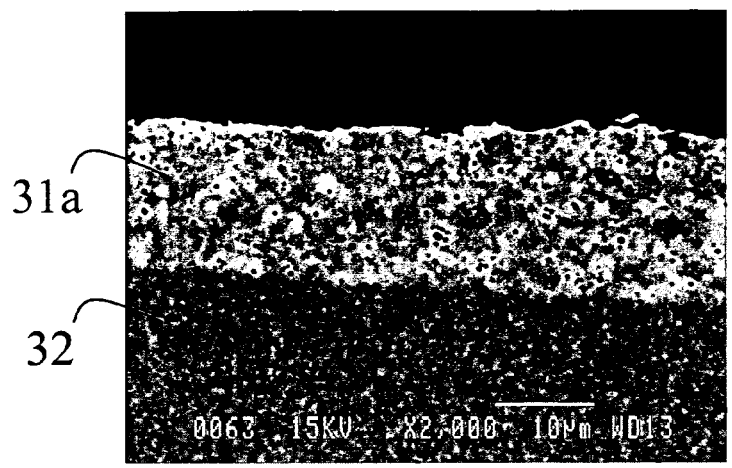
I
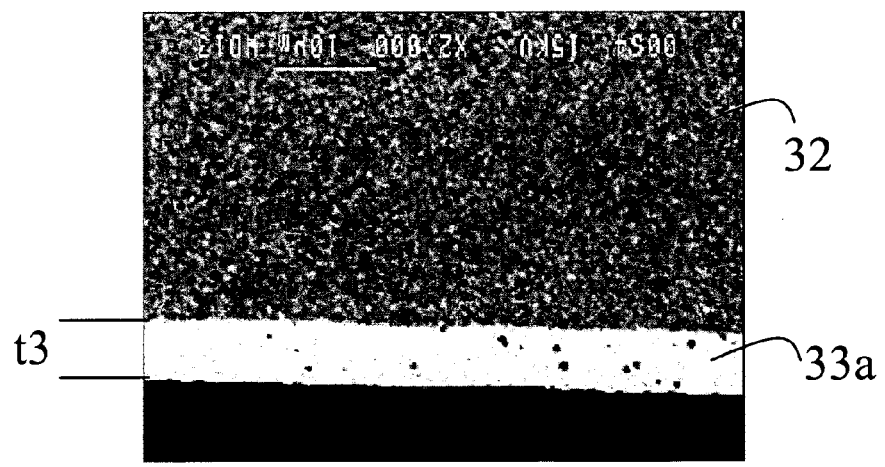
II
Fig. 2b:1

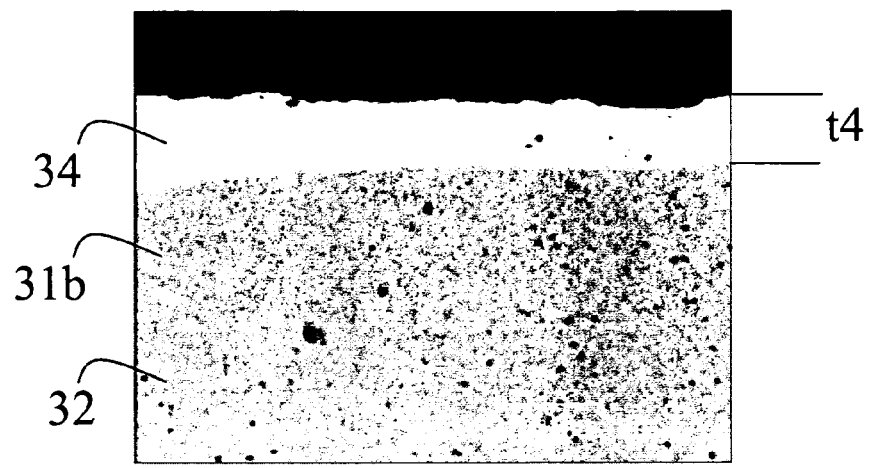
III
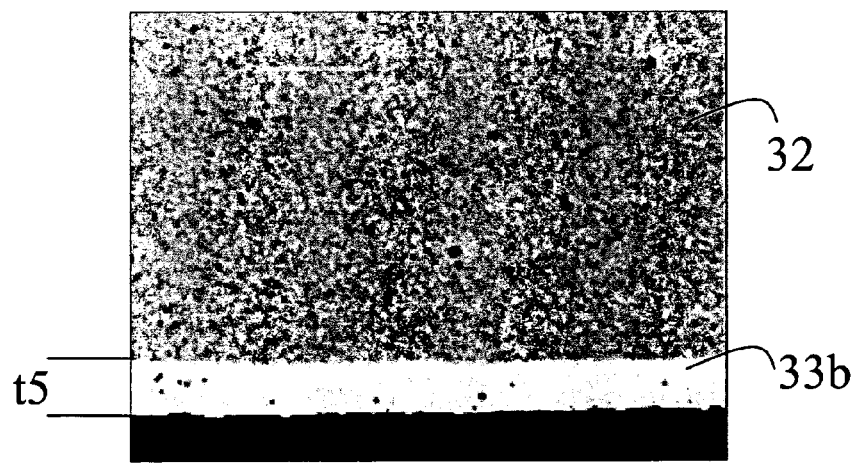
IV
Fig. 2b:2

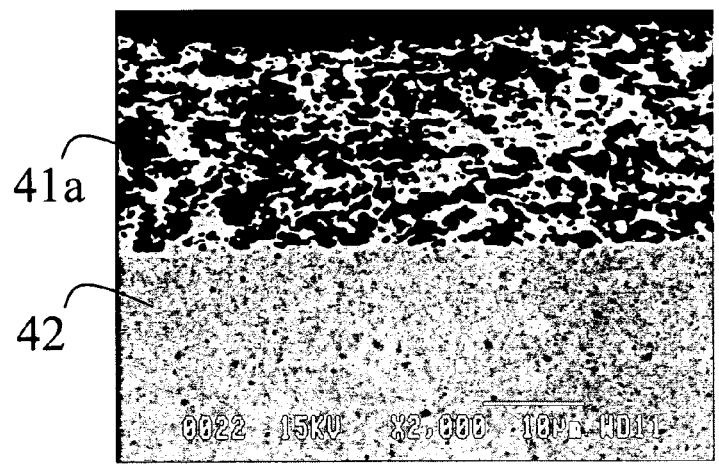
I
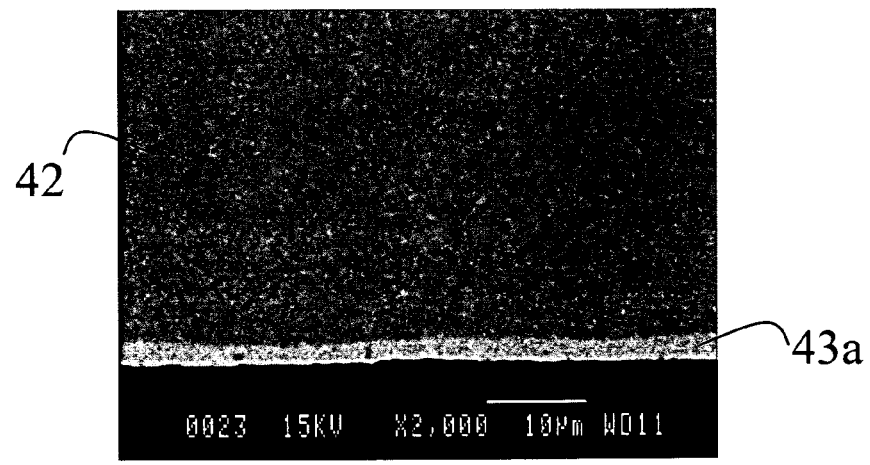
II
Fig. 3a:1

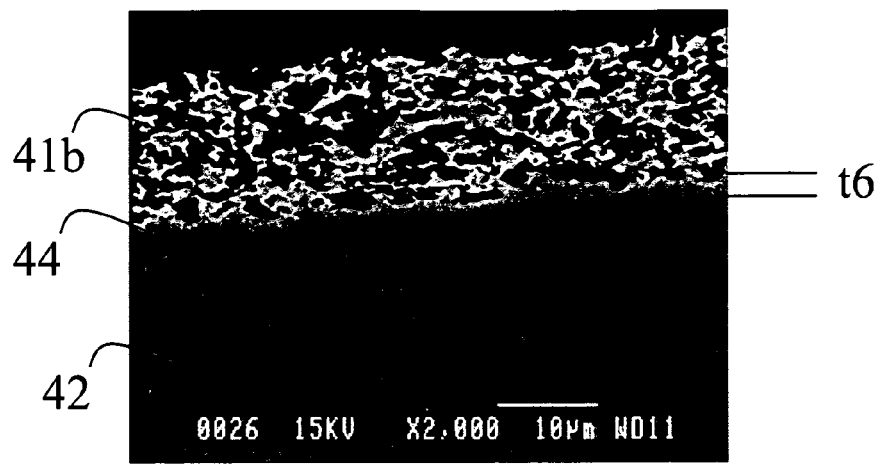
III
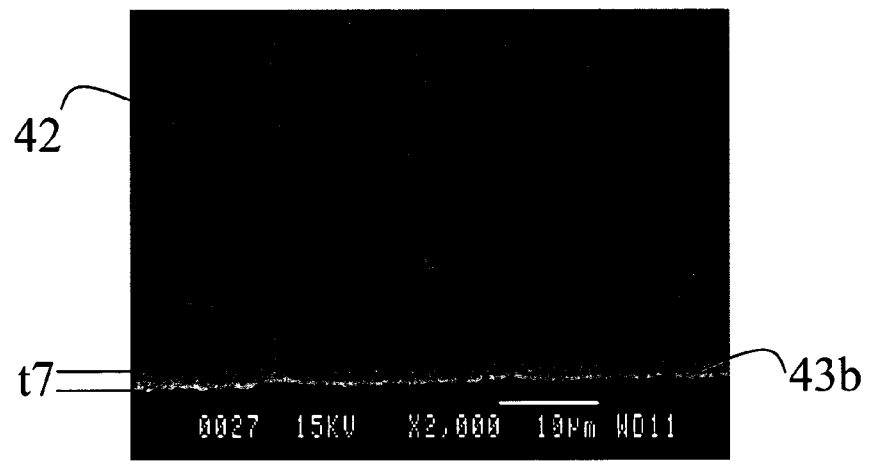
IV
Fig. 3a:2

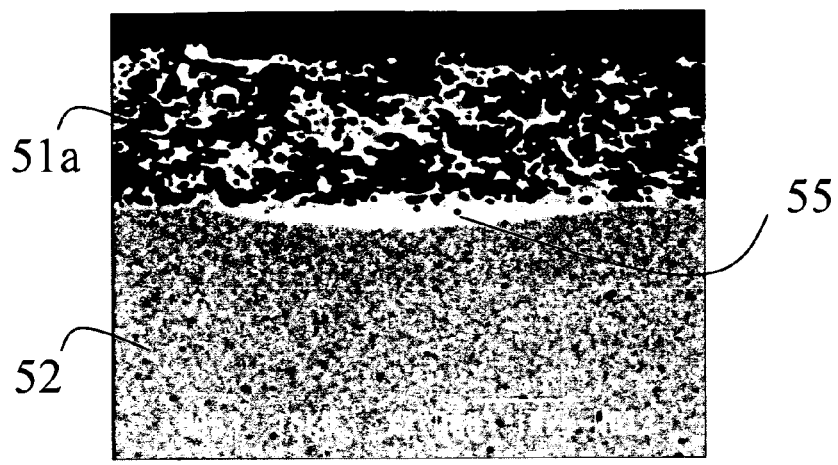
I
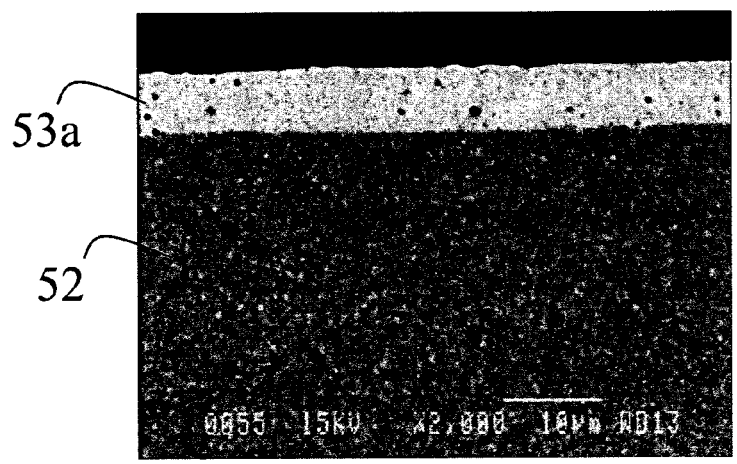
II
Fig. 3b:1

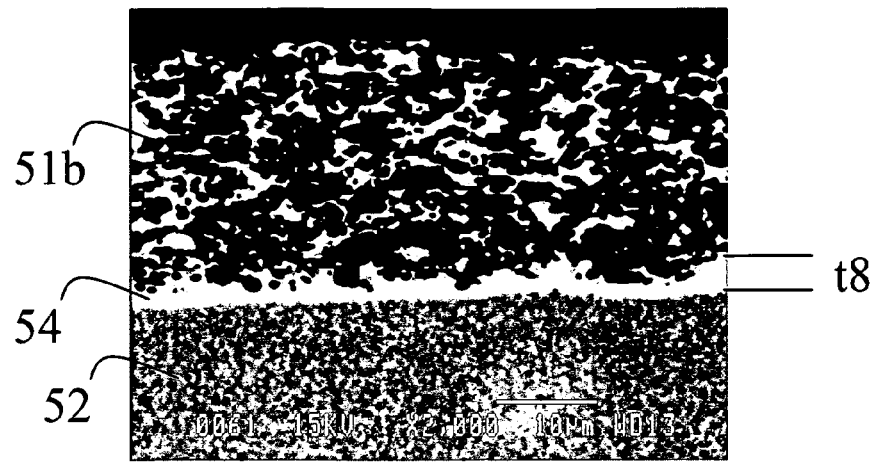
III
IV
Fig. 3b:2

DENTAL APPLICATION COATING

CROSS-REFERENCE TO RELATED APPLICATIONS

This application is a national stage application under 35 U.S.C. §371 of PCT Application No. PCT/EP2010/003636, filed on Jun. 17, 2010, which published in English as WO 2010/145822 A1 on Dec. 23, 2010 and which claims priority benefit of European Patent Application No. 09008015.1, filed on Jun. 19, 2009, the entire contents of which applications and publication are herein incorporated by reference in their entirety.

BACKGROUND

1. Field of the Invention

The present invention relates to a dental application body, comprising an oxide ceramic, containing a bulk material containing an oxide ceramic and at least one coating. Furthermore, the invention relates to a method for producing such a dental application body by providing the bulk material, applying at least one coating, and by sintering the dental application body and the coating.

2. Description of the Related Art

The use of ceramic prostheses in dental application is known for many years, and the applications for sintered products encompass dental implants, bridges, abutments or the like. In general and compared to metal materials, ceramic material have improved properties, in particular with respect to strength, body compatibility, and have usually a color almost like the denture surrounding the implant. A further advantage of ceramic material used as dental implants is its low heat conductivity. Long-term studies, however, reveal that these ceramic materials are subject to aging, and that the fatigue strength of the material is of major importance. Especially when used as an implant replacing molar teeth, the implant has to provide a sufficient resistance to repeated stress over a time period of more than ten years without falling under a specific threshold value for their strength.

Especially when using zirconia ceramics, the effect of the tetragonal to monoclinic transformation of zirconia ceramics stabilized with 3 mol-% yttria has a detrimental effect on aging resistance and has already been investigated. For instance, Jérôme Chevalier et al. have described the significant effect of the presence of a cubic phase in hip prosthesis in the article "Critical effect of cubic phase on aging in 3 mol-%-yttria-stabilized zirconia ceramic for hip replacement prosthesis", issued by Elsevier, Biomaterials, in the year 2004.

Blanks made from zirconium oxide ceramic are for instance disclosed in EP 1 210 054 using a mixture mainly comprising zirconium oxide, and minor amounts of hafnium oxide, yttrium oxide as well as oxides of aluminium, gallium, germanium, indium and the like. These blanks have a pore volume of between 50 and 65% and a pore size in the area of between 0.1 and 3 micrometers. The mixture is preformed into a desired shape, particularly by pressing the material into the blank form, and subsequently sintered in a temperature range of between 850 and 1000° C.

In the field of dental implants, ceramic materials provide the possibility of applying a coating on top of a bulk, wherein this coating has an increased porosity with respect to the bulk material. This more porous structure at the outer surface of the implant provides for a bigger surface, thus resulting in an improved osseointegration of the implant itself.

Among those porous coatings that have been developed or tested by the applicant, certain embodiments showed particularly advantageous results. For example, a specific coating contains zirconium oxide as a main component in some embodiments.

Preventing aging of the dental implant's material is of major importance for the producers of dental implants made of ceramics. Aging may lead to decreased fatigue strength of the implant or at least its surface, possibly resulting in parts of the implant's surface flaking off the implant body.

Tests performed with ceramic bodies coated with a porous outer layer, however, revealed that, under specific circumstances, such coating may lead to an accelerated aging performance of at least the interface between the bulk and a coating.

SUMMARY

Accordingly, certain embodiments of the present disclosure preferably seek to mitigate, alleviate or eliminate one or more deficiencies, disadvantages or issues in the art, such as the above-identified, singly or in any combination by providing an oxide ceramic-based body as a precursor material for dental applications, which has an improved aging capability, and which provides a sufficient strength, especially fatigue strength, over its entire lifetime, even if a porous coating is applied for providing an improved long-term stability.

In certain embodiments, this and other issues are achieved by a dental application body comprising the features of claim 1 and a method for producing this dental application body comprising the features of claim 14. Some preferred embodiments of the disclosure are defined in the respective dependent claims.

According to some embodiments, a dental application body comprising a bulk material containing an oxide ceramic, preferably a zirconium oxide, most preferably a zirconium oxide having a tetragonal microstructure as a main phase, and at least one coating containing an yttrium oxide and/or cerium oxide stabilized zirconium oxide, wherein the content of the stabilizing compounds ($c_{[yttrium\ oxide]}$, $c_{[cerium\ oxide]}$) within the coating with respect to the zirconium oxide (in mol-%) satisfies the formula $c_{[yttrium\ oxide]}+0.6 \times c_{[cerium\ oxide]} \geq 4$.

In some preferred embodiments, the content of the stabilizing compounds $c_{[yttrium\ oxide]}$, $c_{[cerium\ oxide]}$ within the coating with respect to the zirconium oxide (in mol-%) satisfies the formula $c_{[yttrium\ oxide]}+0.6 \times c_{[cerium\ oxide]} \geq 6$.

The coating of some embodiments may be stabilized merely by adding at least 4 mol-% yttrium oxide, preferably at least 6 mol-% yttrium oxide, or by merely adding at least 6.7 mol-% cerium oxide, preferably at least 10 mol-% cerium oxide, or by selecting suitable mixtures of yttrium oxide and cerium oxide, as long as the formula pointing to a desired weighting of both stabilizing compounds is satisfied.

Certain embodiments are based on the perception that ceramic oxide, for instance a zirconium oxide bulk material of a dental implant, can be covered with a preferably porous outer layer without deteriorating the aging resistance of the implant as a whole, as long as the bulk is coated with a coating containing an yttrium oxide and/or cerium oxide stabilized zirconium oxide, as long as the content of cerium oxide and yttrium oxide satisfies the formula $c_{[yttrium\ oxide]}+0.6 \times c_{[cerium\ oxide]} \geq 4$, preferably $c_{[yttrium\ oxide]}+0.6 \times c_{[cerium\ oxide]} \geq 6$.

These stabilized zirconium oxide materials having an yttrium and/or cerium oxide content within the above-mentioned ranges up to now have been considered to be too brittle and not strong enough for dental applications of the kind explained above. However, studies performed by the inventors reveal that providing in certain embodiments, such a coating on top of an oxide ceramic bulk material provide for bodies having the strength and stability sufficient for a body used in dental applications, and at the same time preventing aging characteristics in the dental implant as a whole. In this context, for certain embodiments, the bulk material provides for the overall strength of the body, and the coating applied to the bulk material is suitable to add specific improvements compared to the usual uncoated bodies.

The effect observed in the bodies according to some embodiments is not fully understood yet. However, it is believed that, first of all, a zirconium oxide stabilized with cerium and/or yttrium oxide having a content satisfying the formula $c_{[yttrium\ oxide]} + 0.6 \times c_{[cerium\ oxide]} \geq 4$, preferably $\geq 6$ in some embodiments, can prevent mostly any water molecule penetration into the bulk material, which is considered to be a basic cause for aging of tetragonal zirconia materials, since this chemical composition remains intact without microcracking. Secondly, in some embodiments, cerium and/or yttrium oxide fully stabilized zirconium oxide itself, such as cubic zirconium oxide, is not aging sensitive compared to, e.g., tetragonal zirconium oxide, in particular with respect to aging induced by the biosphere surrounding the ceramic material when used as a dental implant. Thirdly, such zirconium oxide coating in some embodiments provides for a better surface and interface for application of an outer layer on top of the at least one coating.

In general, a dental application body according to certain embodiments, and produced by performing the method according to certain embodiments, provides for a better visual appearance compared to metal dental applications, for an accurate osseointegration, and for a ceramic dental implant with a decreased aging sensitivity, thus having an improved fatigue strength over its entire lifetime.

The bulk material according to certain embodiments, contains an oxide ceramic of the type already known in the prior art. Preferably in some embodiments, the oxide ceramic used for the bulk material contains zirconium oxide, preferably having a tetragonal microstructure, as a main phase. Most preferably in some embodiments, the tetragonal zirconium oxide is an alumina toughened zirconia. Zirconia composite may comprise of about 80% vol or even about 50% of zirconium oxide with 3 mol-% yttrium oxide, and the remaining part mainly comprising aluminium oxide. Alternatively, in some embodiments, the composite comprises zirconium oxide ranging between 50% vol and 100% vol and the remaining portion with aluminium oxide. The compound may be stabilized with ceria.

This results in a bulk material comprising zirconium oxide having an $Y_2O_3$ content of 5.5 weight-% or less in some embodiments.

The term "main phase" can be meant to encompass compositions in which at least 50% and preferably 60%, most preferably more than 75% of the microstructure consist of one single phase having a homogenous chemical composition.

In general, increasing the alumina content of the bulk material results in a stiffer matrix and, thus, in a stronger material. Furthermore, a material having increased alumina content is less prone to aging, since alumina is inert in contact with the environment typically surrounding dental implants. Increasing the alumina content above 50%, however, may lead to a weaker material, since such composite turns to get the characteristics of aluminium oxide, rather than zirconium oxide.

According to some embodiments, at least one coating containing an yttrium oxide and/or cerium oxide stabilized zirconium oxide, wherein the content of the stabilizing compounds $c_{[yttrium\ oxide]}$, $c_{[cerium\ oxide]}$ within the coating with respect to the zirconium oxide (in mol-%) satisfies the formula $c_{[yttrium\ oxide]} + 0.6 \times c_{[cerium\ oxide]} \geq 4$, is applied on top of the bulk material. According to some embodiments, the coating covers at least 50% of the bulk material's surface, preferably more than 75% of the surface. In some highly preferred embodiments, the coating is applied to the surface of the bulk material, which surface during use is in contact with a wet environment.

In some embodiments, the method of producing a coated ceramic body is for instance disclosed in the International Patent Application having the publication number WO 2005/027771 A1 filed by the same applicant, the whole content of which is incorporated herein by reference. It is realised that the subject matter in this publication can be applied for manufacturing and making dental applications in addition to a coating with the herein claimed composition.

In some preferred embodiments, the coating comprises zirconium oxide having a ceria content between 10-20 weight-%, preferably between 12-15 weight-%, based on the zirconium oxide content. In some further preferred embodiments, the coating material comprises up to 50 vol-% of $Al_2O_3$. Furthermore, it is preferred in some embodiments, that the coating material comprises a cerium oxide stabilized zirconium oxide in amounts between 50 and 100 vol-%.

In some embodiments, these compositions preferably provide for a stable cubic phase of the zirconium oxide forming the main member of the coating, and allow for the production of a bulk material providing all improved properties of the dental implant, in particular with respect to fatigue strength, color of the coating and the body as a whole, and for the connection with further outer layers, preferably of those layers having a more porous structure than the bulk and the coating, optionally to be applied on top of the coating, such as hydroxy apatite (HA), bone growth promoting substances (BMP), or other relevant bio substances for promoting osseointegration.

The thickness of the coating according to some embodiments, is not limited to specific ranges as long as the support capacity of the bulk material and the structural integrity of the dental implant are not detrimentally affected. In some preferred embodiments, however, the thickness of the coating lies in the range of between 5 and 300 µm, most preferably between 10 and 150 µm. A coating having a thickness in this preferred range provides in some embodiments, an improved combination of the material properties of the bulk material on the one hand and the coating material on the other hand. In particular, a coating having such a preferred thickness in some embodiments, prevents a substantial moisture penetration into the bulk material and, furthermore, allows for a reliable connection with any further layer on top of the coating.

In some further preferred embodiments, the yttrium oxide and/or cerium oxide stabilized zirconium oxide coating powder forming the basic raw material for the coating has a particle size of between 0.20 and 1.00 µm, preferably between 0.40 and 0.90 µm. Such particle sizes in certain embodiments, allow for an improved and exhaustive sintering reaction within the precursor material when producing the sintered compact without the need of applying sinter regimes (holding time and temperatures) being remarkably different from those applied in the production of other ceramic bodies of the same size.

It is, furthermore, preferred in some embodiments, that if at least one further (outer) layer is applied to the coating, it provides a structure being more porous than the coating. This allows for a better bonding of any outer or top layer onto the body without affecting the improved properties provided by the stabilized zirconium oxide forming the coating on top of the bulk material.

As already mentioned above, oxide ceramics of the kind described above in some embodiments, are pre-shaped and subsequently sintered at elevated temperatures. Precursor materials containing the chemical compositions as set out above are used as a precursor material for a sintered product in some embodiments. The precursor material may comprise a green or pre-sintered body, which is machined, such as by milling, before application of a coating and final sintering. The sintering temperatures to be applied to this precursor material are dependent on the microstructure and the mechanical properties to be achieved. In some preferred embodiments, the sintering temperature for the body according to some embodiments, is in the range of 1300-1600° C., preferably in the range of 1400-1500° C.

In this context, the skilled person is fully aware of the fact that desired reactions within the green compact during sintering, such as phase transformations, in general result from the product of temperature and pressure to be applied to the material, wherein an elevated pressure allows for a decreased sintering temperature, and vice versa. In any case, in certain embodiments, performing the sintering at temperatures within the preferred ranges secures a microstructure of the coating having characteristics desired for the desired application.

The sintering treatment can be accomplished in conventional furnaces at ambient pressure. In some preferred embodiments, however, the precursor material is transformed into the sintered product by applying a sintering and/or hot isostatic pressing treatment in which the sintering is performed while an isostatic elevated pressure being applied onto the precursor material. This allows for a stable connection of the sintered coating on top of the sintered bulk material.

It is to be noted that the sintering treatment can be carried out after applying the coating on top of a non-sintered bulk material. In some preferred embodiments, however, the bulk material is pre-sintered in a first step, and the coating is applied to the pre-sintered bulk body, and subsequently sintered, preferably at temperatures being higher than those already applied in the first pre-sintering step. Furthermore, in some embodiments, the sintering operation is performed taking appropriate sintering temperatures depending on the chemical composition, the thickness of the precursor material and the microstructure and/or strength to be achieved by the sintering treatment into account.

In certain embodiments, the sintered product thus achieved preferably is a precursor material for dental implants. Other applications such as bridges, abutments, crowns or copings etc may be formed having a composition according to some embodiments. Although the details in manufacturing may deviate to some extent due to different desired characteristics. In any case, in some embodiments, performing the sintering of the precursor material preferably leads to a sintered product containing an interface between the bulk material and the coating, thus leading to an improved bonding or connection between the bulk material and the coating, preferably providing a smooth transition from the coating to the bulk material without inner pores or other defects in the boundary between both materials.

The method for the production of a body according to certain embodiments, comprises the steps of providing a bulk material containing an oxide ceramic, preferably a zirconium oxide having a tetragonal microstructure as a main phase, and applying at least one coating containing an yttrium oxide and/or cerium oxide stabilized zirconium oxide, wherein the content of the stabilizing compounds $c_{[yttrium\ oxide]}$, $c_{[cerium\ oxide]}$ within the coating with respect to the zirconium oxide (in mol-%) satisfies the formula $c_{[yttrium\ oxide]}+0.6\times c_{[cerium\ oxide]} \geq 4$, preferably $\geq 6$.

Performing these method steps in certain embodiments, will lead to a dental application body as a precursor material for a sintered product providing the advantageous properties and property combinations already discussed above.

In some preferred embodiments of the method, the bulk material is preformed and subsequently sintered. In a further step, the coating is applied to the sintered bulk body by, firstly, providing a slurry containing the coating material and, secondly, spraying this slurry onto the bulk's surface, followed by a drying treatment. In some highly preferred embodiments, the coating is applied to the bulk in a series of alternating spraying and drying steps, until the desired thickness of the coating is reached.

BRIEF DESCRIPTION OF THE DRAWINGS

The disclosure will be explained in more detail below with reference to the appending Figures showing the results of tests performed with example samples. These Figures are not considered to be limiting for the disclosure, but are given for illustrative purposes only.

FIGS. 2a:1-2a:2 are synopses of four SEM micrographs from two samples showing the intermediate results after 6 weeks of a long term aging test applied to bulk material each having a substantially dense outer layer with different contents of yttrium oxide.

FIGS. 2b:1-2b:2 are synopses of four SEM micrographs from two samples showing the results after 12 weeks of a long term aging test applied to bulk material each having a substantially dense outer layer with different contents of yttrium oxide.

FIGS. 3a:1-3a:2 are synopses of four SEM micrographs from two samples showing the intermediate results of a long term aging test after 6 weeks applied to bulk material each having a porous outer layer with different contents of yttrium oxide.

FIGS. 3b:1-3b:2 are synopses of four SEM micrographs from two samples showing the results after 12 weeks of a long term aging test applied to bulk material each having a porous outer layer with different contents of yttrium oxide.

DETAILED DESCRIPTION

Figure 1A:
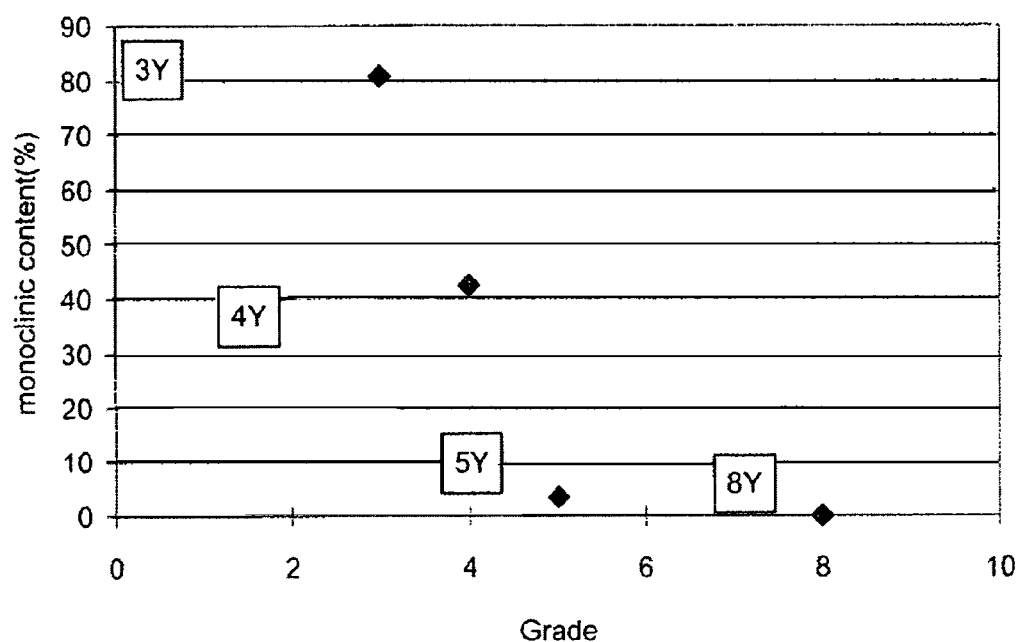
FIG. 1a is a diagram showing the monoclinic content (%) of distinct samples subjected to aging test dependent on the amount of doping the zirconia (zirconium oxide) base material with yttria (yttrium oxide)

Material samples having the compositions given in Table 1 below have been produced and were tested with respect to their density, strength, and aging characteristics.

TABLE 1

| Material No. | Bulk Material | Coating Material | Sintering temperature (° C.) | HIP temperature (° C.) |
|---|---|---|---|---|
| 1-reference | Zirconium oxide, stabilized with 3 mol-% yttrium oxide | Zirconium oxide, stabilized with 3 mol-% yttrium oxide, dense | 1400 | 1400 |
| 2-reference | Zirconium oxide, stabilized with 3 mol-% yttrium oxide | Zirconium oxide, stabilized with 3 mol-% yttrium oxide, porous | 1400 | 1400 |
| 3-example 1 | Zirconium oxide, stabilized with 3 mol-% yttrium oxide | Zirconium oxide, stabilized with 6 mol-% yttrium oxide, dense | 1400 | 1400 |
| 4-example 2 | Zirconium oxide, stabilized with 3 mol-% yttrium oxide | Zirconium oxide, stabilized with 6 mol-% yttrium oxide, porous | 1400 | 1400 |
| 5-example 13 | ATZ (available from INCERCO, USA) | 80 vol-% of zirconium oxide stabilized with 6 mol-% yttrium oxide, 20 vol-% aluminium oxide, porous or dense | 500 | 1500 |
| 6-example 4 | 20 vol-% of zirconium oxide stabilized with 3 mol-% yttrium oxide, 80 vol-% aluminium oxide | 20 vol-% of zirconium oxide stabilized with 6 mol-% yttrium oxide, 80 vol-% aluminium oxide, porous or dense | 1500 | 1500 |
| 7-example 5 | 50 vol-% of zirconium oxide stabilized with 12 mol-% yttrium oxide, 50 vol-% aluminium oxide | 50 vol-% of zirconium oxide stabilized with 12 mol-% yttrium oxide, 50 vol-% aluminium oxide, porous or dense | 1500 | 1500 |
| 8-example 6 | Zirconium oxide stabilized with 12 mol-% yttrium oxide | Zirconium oxide stabilized with 12 mol-% yttrium oxide, porous or dense | 1400 | 1400 |
| 9-example 7 | 50 vol-% of zirconium oxide stabilized with 3 mol-% yttrium oxide, 50 vol-% aluminium oxide | 50 vol-% of zirconium oxide stabilized with 6 mol-% yttrium oxide, 50 vol-% aluminium oxide, porous or dense | 1500 | 1500 |

All material samples were sintered at the given temperatures and ground, and visually examined by using an electron microscope. Furthermore, the material samples were examined with respect to their microstructure, their density of the bulk material, and with respect to their strength in a biaxial strength test.

Furthermore, all material samples were subjected to aging tests, wherein one sample was tested in hot water having a temperature of about 140° C. over a time of 24 hours, the other one (long-term) being conducted in hot water having an elevated temperature of about 90° C. over a time period of 6 weeks. The microstructures of the material samples were investigated in order to evaluate their content of monoclinic microstructure which was expected to originate from a phase transition from tetragonal to monoclinic, and which is considered to be an indication for the amount of aging which took place in the material sample in the course of the aging tests. A second investigation was conducted after a time period of 12 weeks under the same conditions.

FIG. 1a illustrates a diagram showing the monoclinic content (%) of distinct test samples subjected to the first aging test dependent on the amount of doping of the zirconia base material with yttrium oxide. The powders were compacted at uni-axially applied pressure of 700 kg/cm$^2$ and sintered at a temperature of 1500° C. over 2 hours, resulting in a fully tetragonal structure of the sintered samples. The aging test conditions comprised immerging the samples into hot water of a temperature of about 140° C. for 24 hours. The test samples were dried, surface ground and etched in order to perform a microstructure inspection. The amount of aging realised in each sample coincides with the amount of monoclinic phase within each sample resulting from a phase transformation from tetragonal to monoclinic. As a consequence, in general, samples showing a small monoclinic phase content have been considered as not being aging sensitive, whereas those samples having an increased content of monoclinic phase within their microstructures were considered as having a decreased aging resistance. The diagram refers to the grade of the yttrium oxide stabilized zirconia, in which grade 4 coincides with an yttrium content of about 4 mol-%, grade 5 coincides with an yttrium content of about 5 mol-%, and so on. The diagram shows that an yttria content of 3 mol-% leads to an amount of monoclinic phase after the aging test of 80.8%, an yttria content of 4 mol-% leads to an amount of monoclinic phase after the aging test of 42.4%, an yttria content of 5 mol-% leads to an amount of monoclinic phase after the aging test of 3.5%, and that an yttria content of 8 mol-% or more leads to an amount of monoclinic phase after the aging test of 0%. For the purposes of certain embodiments, an yttrium content of at least 4 mol-% is desired, since such doping of the zirconia base material leads to a remarkably decreased phase transformation within the material at elevated temperatures, thus demonstrating an improved aging resistance.

Tests on the basis of this finding finally resulted in the teaching according to some embodiments, that the content of yttrium oxide used for stabilizing a zirconia base material is 6 mol-% in order to suppress the aging within a bulk material 2 in a sufficient manner. For samples A-D, and first batch of samples was prepared, wherein each sample had a first type of outer layer. For samples E-H, a second batch of samples was prepared, wherein each sample had a second type of outer layer. Also, for each batch the outer layer had different amounts of doping material. The outer layer of the first batch was denser than the outer layer of the second batch. The first outer layer is referred to as a dense layer, meaning that it was denser than the second outer layer. Correspondingly, the second outer layer is referred to as a porous outer layer, meaning that it was more porous than the first outer layer. For each batch, simulated aging was performed for 6 weeks and 12 weeks, respectively.

Figure 1B:
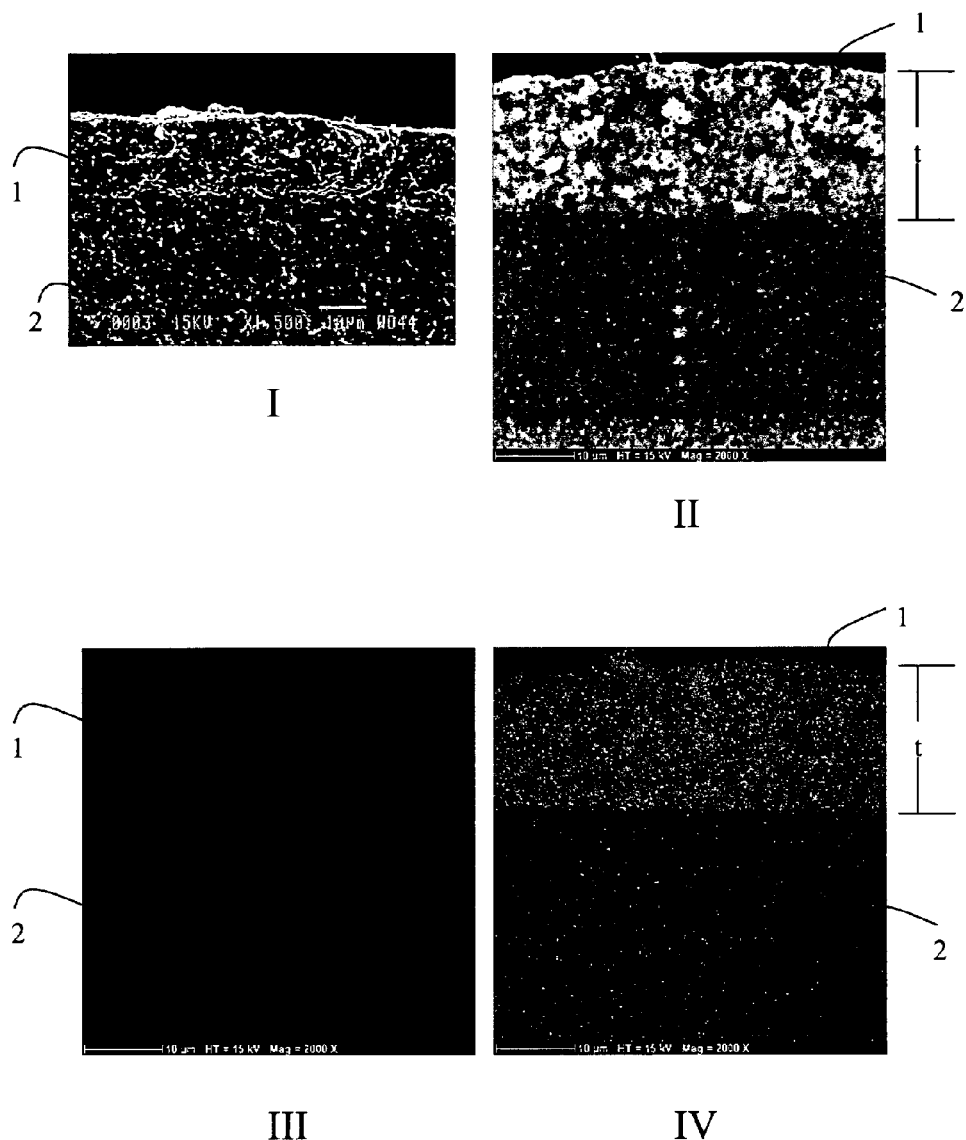
FIG. 1b is a synopsis of four pictures of a sample of a bulk material 2 comprising a zirconia stabilized with 3 mol-% yttrium oxide before simulated aging test.

FIG. 1b comprises four pictures of a sample of a bulk material 2 comprising a zirconia stabilized with 3 mol-% yttrium oxide. The bulk material 2 is coated with a substantially dense outer layer 1 comprising a zirconia stabilized with 6 mol-% yttrium oxide. The sample of FIG. 1b corresponds to material No. 3 in table 1. Pictures I and II show different resolutions of SEM pictures of the sample. Pictures III and IV are EDX mappings of the sample, wherein picture III show the relative zirconium content of the sample and picture IV show the relative yttrium content of the sample. As can be seen in picture II, the substantially dense outer layer has a thickness t, as can be seen in difference in brightness in said layer 1. The thickness can also be seen in picture IV, also evident from the difference in brightness. The sample of FIG. 1b has not been exposed to simulated aging and is comparable to the samples of FIGS. 2a and 2b before aging.

FIGS. 2a:1-2a:2 are synopses of four SEM micrographs from two samples of the first batch, sample A and sample B, showing the intermediate results of a long term aging test (after 6 weeks) applied to bulk material 22 each having a substantially dense outer layer 21a, 21b with different contents of yttrium oxide. The bulk material 22 of sample A (FIG. 2a:1, pictures I and II) is a zirconia stabilized with 3 mol-% yttrium oxide. The substantially dense outer layer 21a of sample A is a zirconia stabilized with 6 mol-% yttrium oxide. Sample A corresponds to material No. 3 in table 1. In contrast to the composition according to sample A, sample B, which is used as a reference, (FIG. 2a:2, pictures III and IV) has a bulk material 22 comprising a zirconia stabilized with 3 mol-% yttrium oxide, and a substantially dense outer layer 21b containing 3 mol-% yttrium oxide as well. Sample B corresponds to material No. 1 of table 1. All pictures I to IV of FIGS. 2a:1-2a:2 show micrographs of samples A and B being subjected to the same simulated aging treatment performed by immerging the samples into hot water having an elevated temperature of about 90° C. for 6 weeks. In both samples A and B, the substantially dense outer layer 21a, 21b is applied to the upper side of the bulk material 22, as shown in pictures I and III, and no dense outer layer 21a, 21b is applied to the bulk material's 22 bottom side, as shown in pictures II and IV. Hence, the bottom side of the bulk material 22 was directly exposed to the water having the elevated temperature, whereas the bulk material 22 was protected from the water of elevated temperature at the upper side of the sample.

When comparing pictures I and II of FIG. 2a:1, it is evident that the bulk material 22 on the upper side (picture I) at the interface between the substantially dense outer layer and the bulk material 22 is continuous darker grey, whereas the bulk material 22 on the bottom side (picture II) that was exposed to the water of elevated temperature appears with a lighter grey layer 23a darker grey further away from the surface exposed to said water. Further analyses performed with sample A revealed that this difference in brightness shows that phase transformation took place in the lighter grey area, i.e. at the bulk material's 22 bottom side. In contrast hereto, substantially no phase transformation appeared in the bulk material's 22 upper side coated with the substantially dense outer layer 21a containing 6 mol-% yttrium oxide. Turning now to pictures III and IV of FIG. 2a:2 illustrating sample B, in picture III the bulk material 22 has a lighter grey layer 24 at the substantially dense outer layer 21b and the bulk material 22 and a darker grey color further away from the substantially dense outer layer 21b. In picture IV, the bulk material 22 on the bottom side that was exposed to the water of elevated temperature has a layer 23b with lighter grey color and is darker grey further away from the surface exposed to said water. Layer 23b and layer 24 have similar colors. Furthermore, the thickness t1 of layer 24 is substantially the same as the thickness t2 of layer 23b. Hence, it is evident that a phase transformation took place in the substantially dense outer layer 21b, which is shown by layer 24. Furthermore, the amount of phase transformation in the substantially dense outer layer 21b and, thus, aging is comparable irrespectively whether the bulk material 22 is protected by a substantially dense outer layer 21b containing 3 mol-% yttrium oxide.

As a result of the analysis of the pictures of FIGS. 2a:1-2a:2, it can be concluded that the phase transformation from tetragonal to monoclinic microstructure of the bulk material 22 is substantially not deferred by covering the bulk material 22 with the substantially dense outer layer 21b comprising zirconia having an yttrium oxide content of 3 mol-% (sample B, pictures III and IV) since the substantially dense layer is prone to aging as such, whereas more or less no aging of the bulk material 22 induced by the water of elevated temperature can be observed when covered by the substantially dense outer layer 21a comprising an yttria stabilized zirconia having an yttrium oxide content of 6 mol-% (sample A, picture I), although such aging actually takes place in the bulk material's 22 bottom side (picture II) directly exposed to the water of elevated temperature. Hence, the aging test indicates that for some embodiments with the latter coating, initiation of aging is at least deferred. In some embodiments of the substantially dense outer layer 21a, 21b is a surface coating.

FIGS. 2b:1-2b:2 are synopses of four micrographs from two samples, sample C and sample D of the first batch, showing the final results of a long term aging test (after 12 weeks). In this test, the same bulk material and substantially dense outer layer as in FIG. 2a:1-2a:2 was used and exposed to a prolonged simulated aging. Hence, the bulk material 32 of sample C and sample D each has a substantially dense outer layer 31a, 31b with different contents of yttrium oxide. The bulk material 32 of sample C (pictures I and II) is a zirconia stabilized with 3 mol-% yttrium oxide. The substantially dense outer layer 31a of sample C is a zirconia stabilized with 6 mol-% yttrium oxide. Sample C corresponds to material No. 3 in table 1. Sample D (pictures III and IV) has a bulk material 32 comprising a zirconia stabilized with 3 mol-% yttrium oxide, and a substantially dense outer layer 31b comprising is a zirconia stabilized with 3 mol-% yttrium oxide as well. Sample D corresponds to material No. 1 of table 1. All pictures I to IV of FIG. 2b:1-2b:2 show micrographs of samples C and D being subjected to the same simulated aging treatment performed by immerging the samples into hot water having an elevated temperature of about 90° C. for 12 weeks. In both samples C and D, the substantially dense outer layer 31a, 31b is applied to the upper side of the bulk material 32, shown in pictures I and III, and no dense outer layer 31a, 31b is applied to the bulk material's 32 bottom side, shown in pictures II and IV. Hence, the bottom side of the bulk material 32 was directly exposed to the water having the elevated temperature.

When comparing pictures I and II, it is evident that the bulk material 32 on the upper side (picture I) at the interface between the substantially dense outer layer and the bulk material 32 is dark grey, whereas the bulk material 32 on the bottom side (picture II) that was exposed to the water of elevated temperature has layer 33a with a lighter grey color and a substantially uniform thickness t3, and is darker grey further away from the surface exposed to said water. Further analyses performed with sample C revealed that phase transformation took place in the bulk material's 32 bottom side whereas substantially no phase transformation took place in the bulk material 32 that was protected by the substantially dense outer layer 31a containing 6 mol-% yttrium oxide. Turning now to pictures III and IV of FIG. 2b:2 showing sample D, in picture III layer 31b protecting the bulk material 32 from the water of elevated temperature has a layer 34 having a thickness t4 and a lighter grey color and is darker grey further away from the surface of layer 31b. In picture IV, the bulk material 32 on the bottom side that was exposed to the water of elevated temperature has a lighter grey layer 33b with a thickness t5 and is darker grey color further away from the surface exposed to said water. Layer 34 and layer 33b have substantially the same color and thickness t4, t5. Hence, it is evident that a phase transformation took place in the bulk material 32 protected by substantially dense outer layer 31b as well as the surface that was directly exposed to said water. Hence, the amount of phase transformation and, thus, aging is comparable irrespectively whether the bulk material is coated by the substantially dense outer layer 31b comprising a zirconia stabilized with 3 mol-% yttrium oxide or not.

As a result of the analysis of the pictures of FIGS. 2b:1-2b:2, it can be concluded that the phase transformation from tetragonal to monoclinic microstructure of the bulk material 32 is substantially not deferred by covering the bulk material 32 with the substantially dense outer layer 31b comprising zirconia having an yttrium oxide content of 3 mol-% (sample D, pictures III and IV), whereas more or less no aging of the bulk material 32 induced by the water of elevated temperature can be observed when the bulk material 32 is covered by the substantially dense outer layer 31a comprising an yttria stabilized zirconia having an yttrium oxide content of 6 mol-% (sample C, picture I), although such aging actually takes place in the bulk material's 32 bottom side (Sample C, picture II) exposed to the water of elevated temperature, which does not have any dense outer layer at all and is directly exposed to said water. Hence, the prolonged aging test of 12 weeks confirms that for some embodiments with the latter coating, initiation of aging is at least deferred. In some embodiments of the substantially dense outer layer 31a, 31b is a surface coating. By comparing the sample in FIG. 1b not exposed to aging with sample C of FIG. 2b:1, the difference in brightness in the layer 1, 31a and the bulk material 2, 32 is substantially the same. Hence, this difference is not attributed to the simulated aging.

FIGS. 3a:1-3a:2 are synopses of four SEM micrographs from two samples of the second batch, sample E and sample F, showing the intermediate results of a long term aging test (after 6 weeks) applied to bulk material 42 each having a porous outer layer 41a, 41b with different contents of yttrium oxide. The bulk material 42 of sample E (FIG. 3a:1, pictures I and II) is a zirconia stabilized with 3 mol-% yttrium oxide. The porous outer layer 41a of sample E is a zirconia stabilized with 6 mol-% yttrium oxide. Sample E corresponds to material No. 4 of table 1. In contrast to the composition according to sample E, sample F (FIG. 3a:2, pictures III and IV) has a bulk material 42 comprising a zirconia stabilized with 3 mol-% yttrium oxide, and a porous outer layer 41b containing 3 mol-% yttrium oxide as well. Sample F corresponds to material No. 2 of table 1. All pictures I to IV of FIGS. 3a:1-3a:2 show micrographs of samples E and F being subjected to the same simulated aging treatment performed by immersing the samples into hot water having an elevated temperature of about 90° C. for 6 weeks. In both samples E and F, the porous outer layer 41a, 41b is applied to the upper side of the bulk material 42, as shown in pictures I and III, and no porous outer layer 41a, 41b is applied to the bulk's 42 bottom side, as shown in pictures II and IV. Hence, the bottom side of the bulk material 42 was directly exposed to the water having the elevated temperature, whereas the bulk material 42 was partly protected from the water of elevated temperature at the upper side of the sample.

When comparing pictures I and II of FIG. 3a:1, it is evident that the bulk material 42 on the upper side (picture I) at the interface between the porous outer layer and the bulk material 42 is continuous darker grey, whereas the bulk material 42 on the bottom side (picture II) that was exposed to the water of elevated temperature appears in darker grey color with a lighter grey layer 43a. Further analyses performed with sample E revealed that this difference in brightness shows that phase transformation took place in the lighter grey area, i.e. at the bulk material's 42 bottom side. In contrast hereto, substantially no phase transformation appeared in the bulk material's 42 upper side coated with the porous outer layer 41a containing 6 mol-% yttrium oxide. Turning now to pictures III and IV of FIG. 3a:2 illustrating sample F, in picture III the bulk material 42 has a lighter grey layer 44 with a thickness t6 at the interface between the porous outer layer 41b and the bulk material 42 and a darker grey color further away from the porous outer layer 41b. In picture IV, the bulk material 42 on the bottom side that was exposed to the water of elevated temperature has a layer 43b with a thickness t7 and a lighter grey color and is darker grey further away from the surface exposed to said water. Layer 43b and layer 44 have similar colors. Furthermore, the thickness of layer 44 is substantially the same as the thickness of layer 43b. Hence, it is evident that a phase transformation took place in the bulk material 42 at the surface directly exposed to said water, which is shown by layer 43b, as well as in the bulk material 42 partly protected by porous outer layer 41b, which is shown by layer 44. Furthermore, the amount of phase transformation in the bulk material 42 and, thus, aging is comparable irrespectively whether the bulk material is partly protected by a porous outer layer 41b containing 3 mol-% yttrium oxide.

As a result of the analysis of the pictures of FIGS. 3a:1-3a:2, it can be concluded that the phase transformation from tetragonal to monoclinic microstructure of the bulk material 42 is substantially not prevented by covering the bulk material 42 with the porous outer layer 41b comprising zirconia having an yttrium oxide content of 3 mol-% (sample F, pictures III and IV), whereas more or less no aging of the bulk material 42 induced by the water of elevated temperature can be observed when covered by the porous outer layer 41a comprising an yttria stabilized zirconia having an yttrium oxide content of 6 mol-% (sample E, picture I), although such aging actually takes place in the bulk material's 42 bottom side (picture II) directly exposed to the water of elevated temperature. Hence, the aging test indicates that for certain embodiments with the latter coating, initiation of aging is at least deferred. In some embodiments of the porous outer layer 41a, 41b is a surface coating.

FIGS. 3b:1-3b:2 are synopses of four micrographs from two samples of the second batch, showing the final results of a long term aging test (after 12 weeks). In this test, the same bulk material and porous outer layer as in FIG. 3b:1-3b:2 was used and exposed to a prolonged simulated aging. Hence, the bulk material 52 of sample G and sample H each has a porous outer layer 51a, 51b with different contents of yttrium oxide. The bulk material 52 of sample G (pictures I and II) is a zirconia stabilized with 3 mol-% yttrium oxide. The porous outer layer 51a of sample G is a zirconia stabilized with 6 mol-% yttrium oxide. Sample G corresponds to material No. 4 of table 1. Sample H (pictures III and IV) has a bulk material 52 comprising a zirconia stabilized with 3 mol-% yttrium oxide, and a porous outer layer 51b comprising is a zirconia stabilized with 3 mol-% yttrium oxide as well. Sample H corresponds to material No. 2 of table 1. All pictures I to IV of FIGS. 3b:1-3b:2 show micrographs of samples G and H being subjected to the same simulated aging treatment performed by immerging the samples into hot water having an elevated temperature of about 90° C. for 12 weeks. In both samples G and H, the porous outer layer 51a, 51b is applied to the upper side of the bulk material 52, shown in pictures I and III, and no porous outer layer 51a, 51b is applied to the bulk material's 52 bottom side, shown in pictures II and IV. Hence, the bottom side of the bulk material 52 was directly exposed to the water having the elevated temperature.

Figure 4:
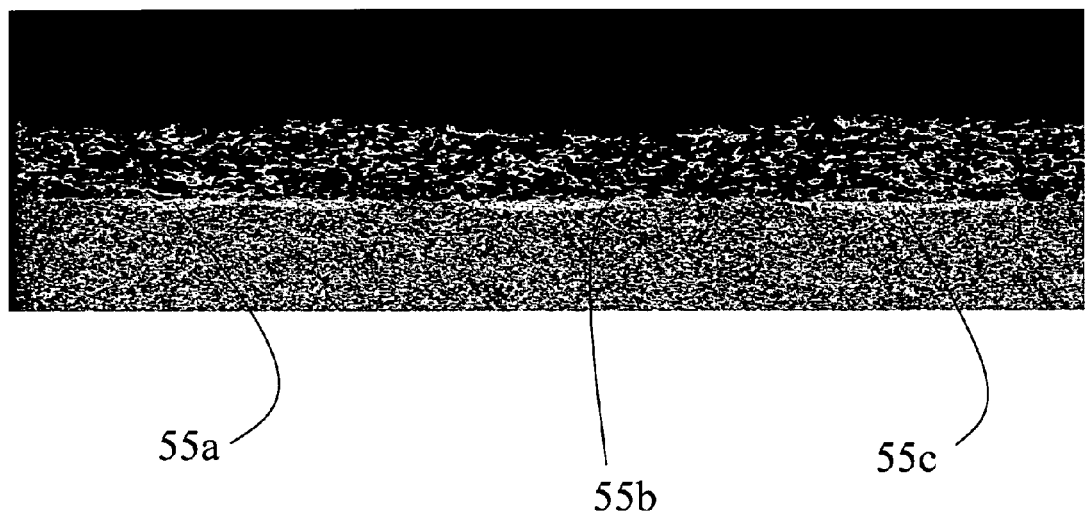
FIG. 4 is an enlarged SEM micrograph of the sample of FIG. 3b:1.

When comparing pictures I and II, it is evident that the bulk material 52 on the upper side (picture I) at the interface between the porous outer layer and the bulk material 52 is dark grey expect for a convex, as seen from the porous outer layer 51a, lighter grey area 55 in the center of picture II whereas the bulk material 52 on the bottom side (picture II) that was exposed to the water of elevated temperature has layer 53a with a lighter grey color and a substantially uniform thickness, and is darker grey further away from the surface exposed to said water. Also, the layer 53a is thicker, as measured from the surface of the sample, than the area 55. Further analyses performed with sample G revealed that this difference in width between area 55 and porous outer layer 53a shows the amount of phase transformation which took place in the bulk material's 52 bottom side is larger than the amount of phase transformation that took place in area 55 of the bulk material 52 that was partly protected by the porous outer layer 51a containing 6 mol-% yttrium oxide. The phase transformation that took place at the interface between the porous outer layer and the bulk material 52 is substantially retarded compared to a zirconia stabilized with 3 mol-% yttrium oxide and a porous outer layer 51b comprising is a zirconia stabilized with 3 mol-% yttrium oxide. This is further illustrated in FIG. 4, where a wider portion of sample G is shown, wherein a plurality of convex areas 55a, 55b, 55c in which phase transformation has occurred at a few local grains acting as seeds for continued phase transformation. Turning now to pictures III and IV of FIG. 3b:2 showing sample H, in picture III the bulk material that was partly protected from the water of elevated temperature has a layer 54 with a thickness t8 and having a lighter grey color towards said layer 51b and is darker grey further away from the surface of said layer 51b. In picture IV, the bulk material 52 on the bottom side that was exposed to the water of elevated temperature has a lighter grey layer 53b with a thickness t9 and a darker grey color further away from the surface exposed to said water. Layer 54 and layer 53b have substantially the same color and thickness t8, t9. Hence, it is evident that a phase transformation took place in the bulk material 52 partly protected by porous outer layer 51b as well as the surface that was directly exposed to said water. Hence, the amount of phase transformation and, thus, aging is comparable irrespectively whether the bulk material is coated by the porous outer layer 51b comprising a zirconia stabilized with 3 mol-% yttrium oxide or not.

As a result of the analysis of the pictures of FIGS. 3b:1-3b:2, it can be concluded that the phase transformation from tetragonal to monoclinic microstructure of the bulk material 52 is not prevented by covering the bulk material 52 with the porous outer layer 51b comprising zirconia having an yttrium oxide content of 3 mol-% (sample H, pictures III and IV), whereas more or less no aging of the bulk material 52 induced by the water of elevated temperature can be observed when the bulk material 52 is covered by the porous outer layer 51a comprising an yttria stabilized zirconia having an yttrium oxide content of 6 mol-% (sample G, picture I), although such aging actually takes place in the bulk material's 52 bottom side (Sample G, picture II) exposed to the water of elevated temperature, which does not have any porous outer layer at all and is directly exposed to said water. Hence, the prolonged aging test of 12 weeks confirms that for certain embodiments with the latter coating, initiation of aging is at least deferred. In some embodiments of the substantially dense outer layer 31a, 31b is a surface coating. In some embodiments of the porous outer layer 51a, 51b is a surface coating.

As can be concluded from some of the above embodiments, a bulk material of a body, comprising an oxide ceramic, such as a zirconium oxide, protective by at least one coating containing an yttrium oxide and/or cerium oxide stabilized zirconium oxide, wherein the content of the stabilizing compound $c_{[yttrium\ oxide]}$, $c_{[cerium\ oxide]}$ within the coating with respect to the zirconium oxide (in mol-%) satisfies the formula $c_{[yttrium\ oxide]} + 0.6 \times c_{[cerium\ oxide]} \geq 4$ can at least defer initiation of aging.

It can also be concluded from some of the above embodiments that the deferment of initiation is dependent on the porosity of the coating or layer. A denser coating or layer can defer the initiation of the aging more than a more porous layer or coating having the same material composition.

A dental application body according to certain embodiments of the disclosure is useful in applications wherein aging is an issue. Such aging can for example be relevant for clinical use in human tissue, such as bone anchored implant. Such implant may e.g., comprise implants that are subject to loading, e.g., dental implants including the bone anchored dental fixture including, e.g., a threaded structure to anchor the implant. In such applications, it may be desired to at least defer initiation of aging, such as beyond what is clinically relevant. What is clinically relevant depends on the actual application. As has been discussed above, the porosity of the coating or layer on top of the bulk material can be used to control the deferment of the initiation of the aging.

The present invention has been described above with reference to specific embodiments. However, other embodiments than the above described are equally possible within the scope of the invention. The different features and steps of the invention may be combined in other combinations than those described. The scope of the invention is only limited by the appended patent claims.

What is claimed is:

1. A dental application body comprising:
a bulk material containing an oxide ceramic, and
at least one coating containing a stabilizing compound, the stabilizing compound containing at least one of an yttrium oxide stabilized zirconium oxide or a cerium oxide stabilized zirconium oxide, wherein the content of the stabilizing compound $c_{[yttrium\ oxide]}$, $c_{[cerium\ oxide]}$ within the coating with respect to the zirconium oxide (in mol-%) satisfies the following formula:

$$c_{[yttrium\ oxide]} + 0.6 \times c_{[cerium\ oxide]} \geq 4,$$

wherein the body comprises at least one layer on top of the coating, and
wherein the at least one layer has an increased porosity with respect to the bulk material and the coating.

2. A dental application body according to claim 1, wherein the content of the stabilizing compound within the coating with respect to the zirconium oxide (in mol-%) satisfies the following formula:

$$c_{[yttrium\ oxide]} + 0.6 \times c_{[cerium\ oxide]} \geq 6.$$

3. A dental application body according to claim 1, wherein the coating comprises yttrium oxide stabilized zirconium oxide, and that the yttrium oxide content within the coating with respect to the zirconium oxide is at least about 6 mol-%.

4. A dental application body according to claim 1, wherein the coating comprises cerium oxide stabilized zirconium oxide, and that the cerium oxide content within the coating with respect to the zirconium oxide is at least about 10 mol-%.

5. A dental application body according to claim 1, wherein the coating comprises zirconium oxide having an $Y_2O_3$ content between about 10 and about 20 weight-% based on the zirconium oxide content.

6. A dental application body according to claim 5, wherein the $Y_2O_3$ content is between about 12 and about 15 weight-% based on the zirconium oxide content.

7. A dental application body according to claim 1, wherein the coating comprises up to about 50 weight-% of $Al_2O_3$.

8. A dental application body according to claim 1, wherein the coating comprises a cerium oxide stabilized zirconium oxide in an amount of up to about 50 weight-%.

9. A dental application body according to claim 1, wherein a thickness of the coating is in a range of between about 5 and about 300 μm.

10. A dental application body according to claim 9, wherein the thickness of the coating is in a range of between about 10 and about 150 μm.

11. A dental application body according to claim 1, wherein the yttrium oxide stabilized zirconium oxide coating has cubic phase as a main phase.

12. A dental application body according to claim 1, wherein the yttrium oxide or cerium oxide stabilized zirconium oxide coating is made from a powder, which has a particle size of between about 0.20 and about 1.00 μm.

13. A dental application body according to claim 12, wherein the particle size is between about 0.40 and about 0.90 μm.

14. A dental application body according to claim 1, wherein the body is a precursor material for at least one of an implant, bridge, abutment, or crown for use in the maxillofacial region.

15. A dental application body according to claim 1, wherein the oxide ceramic comprises zirconium oxide.

16. A method for producing a dental application body comprising:
    providing a bulk material containing an oxide ceramic,
    applying at least one coating containing a stabilizing compound, the stabilizing compound containing at least one of an yttrium oxide stabilized zirconium oxide or a cerium oxide stabilized zirconium oxide, wherein the content of the stabilizing compound $c_{[yttrium\ oxide]}$, $c_{[cerium\ oxide]}$ within the coating with respect to the zirconium oxide (in mol-%) satisfies the following formula: $c_{[yttrium\ oxide]}+0.6\times c_{[cerium\ oxide]}\geq 4$, and
    applying at least one layer on top of the coating,
    wherein the at least one layer has an increased porosity with respect to the bulk material and the coating.

17. A method according to claim 16, wherein the dental application body is subjected to a sintering treatment in order to produce a sintered product, and that the sintering treatment is performed at a sintering temperature in a range of about 1300 to about 1600° C.

18. A method according to claim 16, wherein the oxide ceramic contains a zirconium oxide having a tetragonal microstructure as a main phase.

19. A method according to claim 17, wherein the sintering temperature is in a range of about 1400 to about 1500° C.

* * * * *